(12) United States Patent
Barba

(10) Patent No.: US 8,941,731 B2
(45) Date of Patent: Jan. 27, 2015

(54) SYSTEM AND METHOD TO VERIFY COMPLETE CONNECTION OF TWO CONNECTORS

(75) Inventor: James M. Barba, Farmington Hills, MI (US)

(73) Assignee: Hitachi Automotive Systems Americas, Inc., Harrodsburg, KY (US)

(*) Notice: Subject to any disclaimer, the term of this patent is extended or adjusted under 35 U.S.C. 154(b) by 489 days.

(21) Appl. No.: 13/301,865

(22) Filed: Nov. 22, 2011

(65) Prior Publication Data

US 2013/0128032 A1   May 23, 2013

(51) Int. Cl.
| H04N 7/18 | (2006.01) |
| H04N 9/47 | (2006.01) |
| H01R 13/52 | (2006.01) |
| G01N 21/00 | (2006.01) |
| H01R 13/64 | (2006.01) |
| G02B 6/38 | (2006.01) |
| H04N 1/21 | (2006.01) |

(52) U.S. Cl.
CPC ............. *G01N 21/00* (2013.01); *H01R 13/64* (2013.01); *G02B 6/3895* (2013.01); *H04N 1/2112* (2013.01)
USPC ............ 348/135; 348/82; 439/271; 439/278; 439/283

(58) Field of Classification Search
CPC .... H01R 13/641; H01R 13/639; H01R 13/64; G02B 6/3895; G02B 6/3816; H04N 1/2112
See application file for complete search history.

(56) References Cited

U.S. PATENT DOCUMENTS

| 4,811,002 | A | * | 3/1989 | Otsubo | 340/687 |
| 5,226,679 | A | * | 7/1993 | Klinger | 285/93 |
| 5,499,848 | A | * | 3/1996 | Kujawski | 285/93 |
| 5,676,403 | A | * | 10/1997 | Klinger et al. | 285/93 |
| 5,788,527 | A | * | 8/1998 | Sanders et al. | 439/352 |
| 6,183,020 | B1 | * | 2/2001 | Luft | 285/93 |
| 6,296,508 | B1 | * | 10/2001 | Kuwahara et al. | 439/353 |
| 6,679,724 | B2 | * | 1/2004 | Hillman et al. | 439/489 |
| 6,769,929 | B2 | * | 8/2004 | Saka et al. | 439/352 |
| 2008/0274635 | A1 | * | 11/2008 | Shirai et al. | 439/271 |
| 2010/0127492 | A1 | * | 5/2010 | Poder et al. | 285/93 |

* cited by examiner

*Primary Examiner* — Joseph Ustaris
*Assistant Examiner* — Rebecca Volentine
(74) *Attorney, Agent, or Firm* — Gifford, Krass, Sprinkle, Anderson & Citkowski, P.C.

(57) ABSTRACT

An inspection system which verifies the complete connection of two connectors at an inspection station. An indicator is placed on one of the first and second connectors which becomes hidden from view only when the first and second connectors are in a fully connected position. A camera is positioned at the inspection station which generates an output signal representative of the field of vision of the camera. That camera output signal is coupled to an optical recognition circuit which generates an alarm signal if the indicator is present in the camera image.

6 Claims, 2 Drawing Sheets

SYSTEM AND METHOD TO VERIFY COMPLETE CONNECTION OF TWO CONNECTORS

BACKGROUND OF THE INVENTION

I. Field of the Invention

The present invention relates generally to inspection systems and methods and, more particularly, to a system and method to verify the complete and locked connection of two connectors.

II. Description of Related Art

In mass production environments, such as the manufacture of automotive vehicles, it is often necessary to connect two electrical connectors together as a part of the assembly process. Furthermore, many of these electrical connectors include locking elements which lock and firmly hold the two connectors together once the two connectors are moved to a fully connected position.

For example, in one type of connection between two electrical connectors, one or more flexible locking tabs are attached to one of the electrical connectors which engage cooperating ramps on the other electrical connector. Thus, as the electrical connectors are pushed together from a disconnected and to a fully connected position, the locking tabs flex outwardly due to their coaction with their cooperating ramps on the other connector. When moved to a fully connected position, these locking tabs snap behind an end of the ramp to lock together and prevent disconnection of the two electrical connectors during the operation of the vehicle. However, in the event that the two electrical connectors are not fully connected and locked together, the connectors may separate over time due to vehicle vibration and/or other operating environment factors.

There have been a number of previously known systems and methods to verify the complete connection of the two electrical connectors. For example, in one previously known method, the worker connecting the two connectors together listens for the click of the locking tab upon full connection of the two connectors caused by the locking tab returning to its undeflected position. However, this method has not proven wholly satisfactory since it is often difficult for the worker to hear the click of the locking tab in the oftentimes noisy environment of the manufacturing or assembly environment.

A still further previously known method to verify the complete connection of two connectors is to perform a conductivity test through the two connectors. This method, however, has not proven reliable since, in many cases, the connectors pass the conductivity test even though the connectors are only partially connected together and not fully connected and locked together as desired.

There have also been previously known camera inspection systems that view the engagement of the connector body at an inspection station. However, such previously known camera vision systems have not been completely satisfactory since the tolerances for the body of the two connectors do not allow for 100% accuracy. Similarly, the use of laser marked engagement check lines for camera inspection systems is difficult to apply accurately, also due to the tolerance capability of the laser marking equipment.

SUMMARY OF THE PRESENT INVENTION

The present invention provides both a method and a system which overcome the previously known disadvantages for the inspection of the complete connection of two connectors.

In brief, in the conventional fashion, the first and second connectors are movable relative to each other between a disconnected position and a fully connected and locked position. An indicator is provided on at least one of the first and second connectors which becomes hidden from view only when the connectors are moved to their fully connected and locked position. This indicator may take any of several forms, such as a colored mark, a pattern placed on the connector, etc.

For example, many electrical connectors use at least one flexible locking tab on one connector which engages a ramp on the other connector. When the connectors are moved from their disconnected and toward their connected position, the locking tab flexes outwardly due to its coaction with the ramp on the other connector. However, when the two connectors are moved to their fully connected position, the locking tab snaps over the end of the ramp thus locking the two connectors together. Furthermore, when the two connectors are moved to their fully connected and locked position, the locking tab overlies and thus covers a portion on the end of the ramp of the other connector. Thus, if the indicator is placed on that portion of the end of the ramp, the locking tab will cover the indicator only when the two connectors are in their fully connected and locked position.

An optical camera is positioned at an inspection station for the connectors following assembly. The camera generates an output signal representative of the camera image and provides a signal to an optical recognition circuit.

The optical recognition circuit, upon receipt of the camera signal, determines if the indicator is present within the captured camera image. If so, the optical recognition circuit generates an alarm signal indicative that the first and second connectors are not fully connected and locked together. That alarm signal can be used in many different fashions, such as to reject the connectors, or merely alert personnel to complete the connection of the two connectors.

Although preferably the indicator becomes obscured or covered once the two connectors are moved to their fully connected and locked position, the converse can also be true, i.e. the indicator only becomes visible once the connectors are fully connected and locked together. In this case, the optical recognition circuit would generate an alarm signal only when the indicator is not present in the captured camera image.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 2:
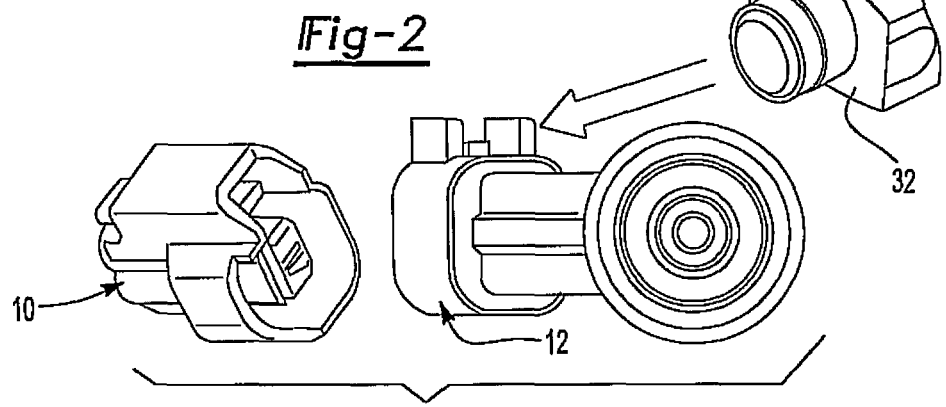
FIG. 2 is an exploded elevational view illustrating the present invention.
Figure 3:
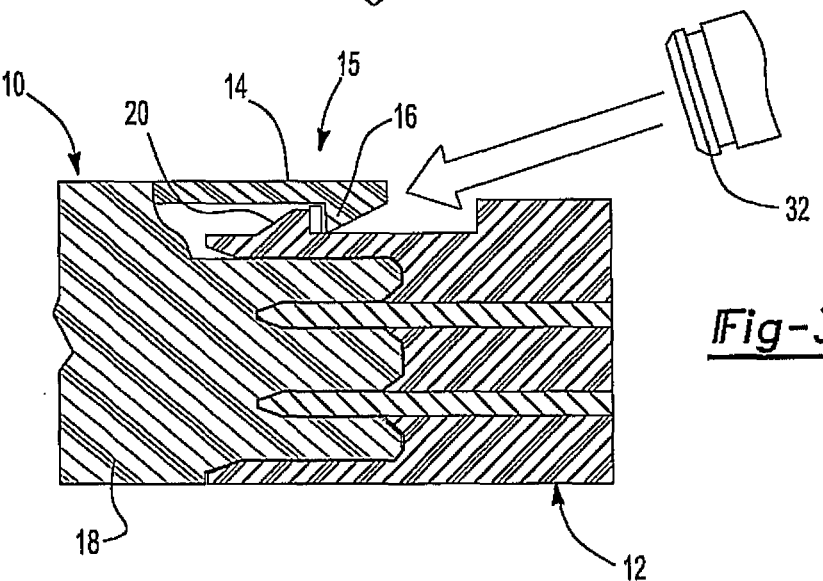
FIG. 3 is a sectional view illustrating two connectors in a fully connected and locked position.
Figure 4:
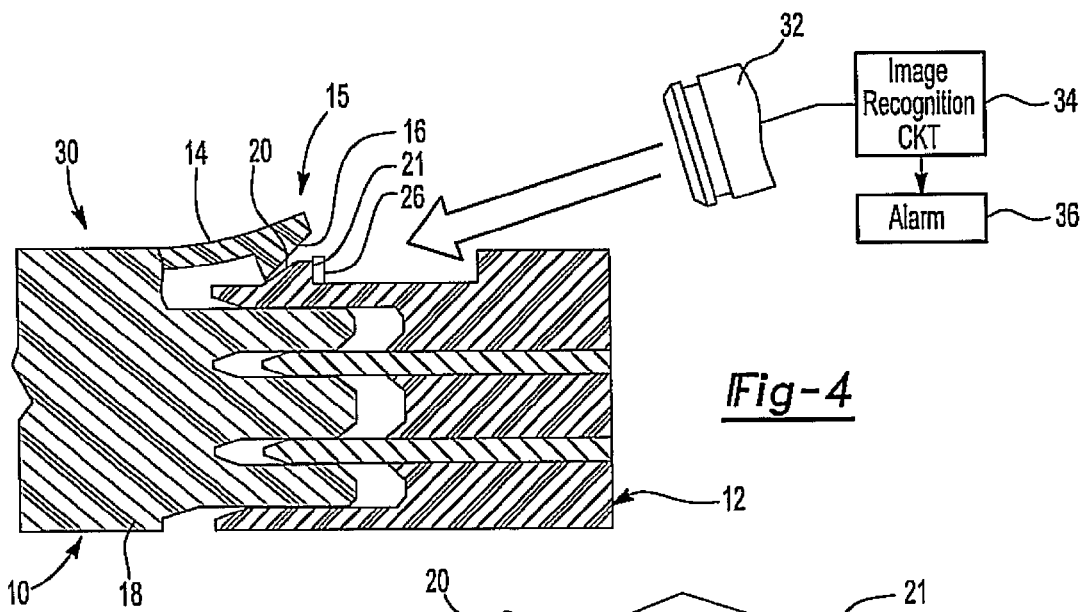
FIG. 4 is a view similar to FIG. 3, but illustrating the two connectors in a partially connected position.

With reference first to FIGS. 2-4, a first electrical connector 10 and a cooperating second electrical connector 12 are illustrated. The connectors 10 and 12 are movable between a disconnected position, illustrated in FIG. 4, and a fully connected and locked position, illustrated in FIG. 3.

The two connectors 10 and 12 also include a locking feature 15 which locks the connectors 10 and 12 together upon movement of the connectors 10 and 12 to their fully connected position. This locking feature ensures that the connectors 10 and 12 will remain in their fully connected position despite being subjected to harsh, high vibration operating environments for extended periods of time.

The locking feature for locking the two connectors 10 and 12 together when in their fully connected position may take many forms. However, the locking feature illustrated in FIGS. 3 and 4 includes a flexible locking tab 14 which is attached to the first connector 10. The locking tab 14 includes a hook 16 at its free end and is typically of a one piece construction with a body 18 of the first connector 10.

As the two connectors 10 and 12 are moved from their disconnected and to their connected position, the hook 16 on the locking tab 14 engages a ramp 20 attached to or formed on the body 22 of the other or second connector 12. The ramp 20, furthermore, is oriented so that, as the connectors 10 and 12 are pushed together toward their fully connected position, the ramp 20 deflects the locking tab 14 outwardly as best shown in FIG. 4. However, when the two connectors 10 and 12 are moved to their fully connected position, the hook 16 of the locking tab 14 passes over an end 24 on the ramp 20. Once this occurs, the resiliency of the locking tab 14 returns the locking tab 14 towards its undeflected state so that the hook 16 overlaps the end 24 of the ramp 20 as shown in FIG. 3. Once this occurs, the mechanical engagement between the locking tab hook 16 and the end 24 of the ramp 20 securely locks the connectors 10 and 12 together in their fully connected position.

Figure 5:
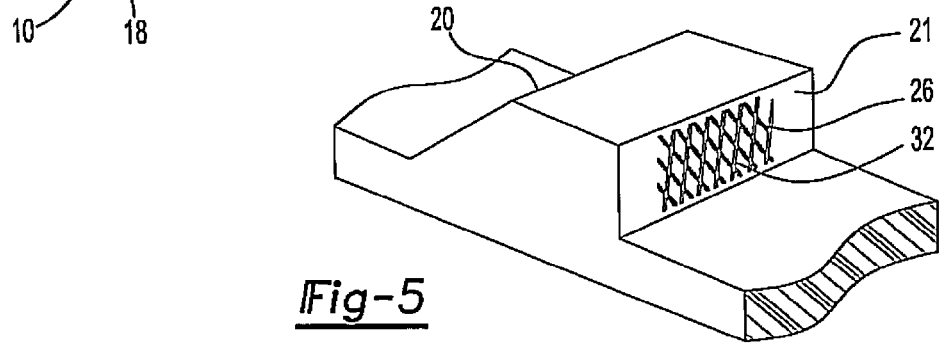
FIG. 5 is a fragmentary view of a portion of one connector.

In order to facilitate the inspection of the connectors 10 and 12 after assembly, as best shown in FIG. 5, an indicator 26 is provided on an end 21 of the ramp 20 that is covered by the hook 16 only when the connectors 10 and 12 are moved to their fully connected and locked position. Consequently, when the connectors 10 and 12 are only partially connected, as shown in FIG. 4, the indicator 26 will be visible. Conversely, when the connectors 10 and 12 are fully connected and locked, the hook 16 of the locking tab 14 overlies the indicator 26 and obscures the indicator 26 from vision.

Figure 6:
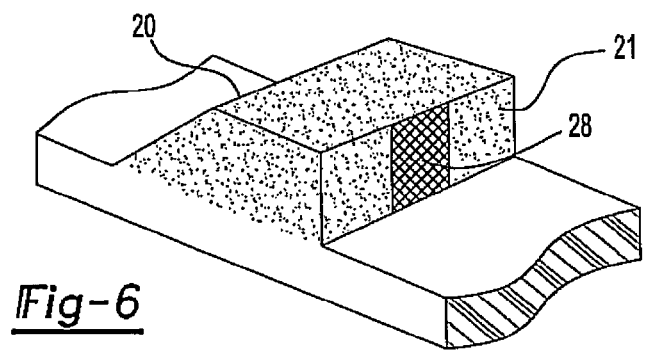
FIG. 6 is a view similar to FIG. 5, but illustrating a modification thereof.
Figure 7:
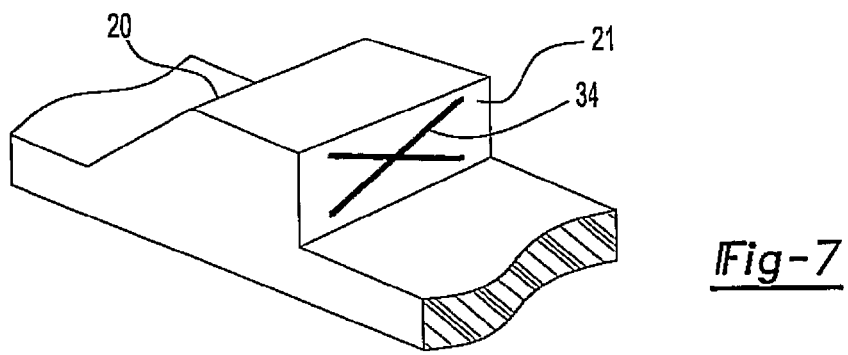
FIG. 7 is a view similar to FIG. 5, but illustrating a still further modification thereof.

The indicator 26 may take any of several different forms. For example, as shown in FIG. 6 the indicator 26 could be an area 28 of color on the connector 12 different from the color of the connector body 22. Alternatively, as shown in FIG. 5, the indicator 26 could be a pattern 32 applied or formed in the connector body 22. Still other types of indicators 26 may be used such as a single mark 34 in FIG. 7 without deviation from the spirit or scope of the invention.

With reference now to FIG. 4, in order to verify the full connection and locking of the connectors 10 and 12, the connectors 10 and 12, after assembly, are moved to an inspection station 30. An optical camera 32 is positioned relative to the inspection station 30 so that an optical image captured by the camera 32 will include the indicator 26, if visible, within the image capture of the camera 32.

The image captured by the camera 32 is coupled as an output signal to an optical image recognition circuit 34 which may be of any conventional construction. The optical recognition circuit 34, which may operate under the control of a programmed processor, such as a microprocessor, identifies the indicator 26, if present. The presence of the indicator 26 is indicative that the connectors 10 and 12 are not in their fully connected and locked position. Consequently, when the optical recognition circuit 34 identifies the indicator 26, the optical recognition circuit 34 generates an output signal to an alarm 36 used to indicate the presence of a connector assembly that is not fully connected and locked together.

The actual alarm 36 may take any conventional form. For example, the alarm 36 could merely sound or illuminate an alarm to alert a worker that the connector assembly is not locked together and enable the worker to complete the locking process for the connector assembly. Alternatively, the alarm 36 could be used to divert the unlocked connector assembly to a separate repair area for the electrical connectors. The alarm can take still further forms.

Since the optical recognition circuit 34 is designed or programmed to locate the indicator 26 anywhere within the field of vision or image capture for the camera 32, even relatively wide tolerances for the connector dimensions will not adversely affect the operation of the overall system. Likewise, the precise position of the connectors 10 and 12 at the inspection station 30 is no longer critical. Instead, it is only necessary that the indicator 26 on the connector 12 be positioned within the field of vision or image capture for the camera 32.

Figure 1:
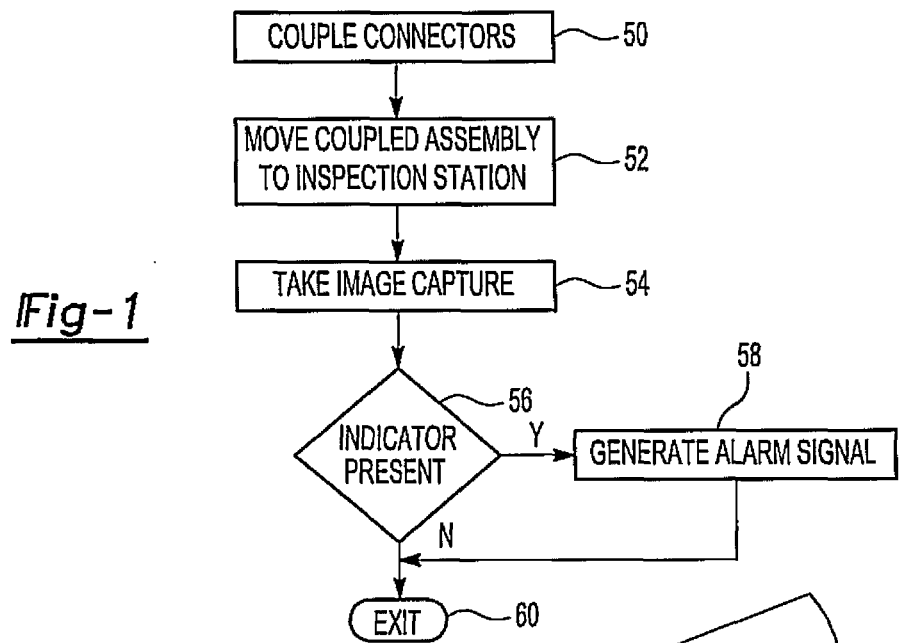
FIG. 1 is a flowchart illustrating the operation of the present invention.

A flowchart illustrating the operation of the present invention is shown in FIG. 1. At step 50, the two connectors 10 and 12 are coupled together either manually or by machine. Step 50 then proceeds to step 52.

At step 52, the connector assembly, i.e. the two connectors 10 and 12 in their assembled or connected position, are moved to an inspection station. Step 52 then proceeds to step 54. At step 54, the camera 32 is activated to take an image capture of the coupled connectors 10 and 12. That image capture 54 is then coupled as an input signal to the optical recognition circuit 34. Step 54 then proceeds to step 56.

At step 56, the optical recognition circuit 34, preferably operating under a software programmed processor, determines if the indicator 26 is present within the captured image. If so, step 56 branches to step 58 and generates an output signal. Otherwise, step 56 proceeds to the exit 60.

Although the present invention has been described as operating so that the locking tab 14 covers or visually obscures the indicator 26 when the connectors 10 and 12 are in their fully coupled and locked position, it will be understood that the system and method of the present invention may operate in the opposite fashion. When operated in the opposite fashion, the indicator 26 becomes visible, i.e. not obscured, only when the connectors are in their fully coupled and locked position. In this case, it is only necessary that the indicator 26 become hidden from view only when the first and second connectors are either in an unlocked partially connected position or in the fully connected and locked position, but not both.

Similarly, although the invention has been described as verifying the fully connected and locked position of two electrical connectors, the invention can be used with other types of connectors, such as fluid connectors.

From the foregoing, it can be seen that the present invention provides a simple yet highly effective inspection system and method to assure and verify the complete connection and locking of two connectors. Having described my invention, however, many modifications thereto will become apparent to those skilled in the art to which it pertains without deviation from the spirit or scope of the invention as defined by the appended claims.

I claim:

1. An inspection system comprising:
    a first and a second connector movable relative to each other between an unlocked partially connected position and a locked fully connected position, an indicator attached to said first connector which becomes hidden from view only when the first and second connectors are in said locked fully connected position, a camera which generates an output signal representative of the appearance of objects present at an inspection station, said camera positioned to detect the indicator, if visible, when the first and second connectors are at the inspection station, and an optical recognition circuit which receives the output signal from the camera, determines if the indicator is visible in the camera output signal and generates an alarm signal if the first and second connectors are in a partially connected position based upon the presence of the indicator in the camera output signal, wherein said indicator comprises a pattern applied to said first connector, wherein the first connector includes a ramp and the second connector includes a flexible and resilient locking tab having a hook which travels along said ramp as said connectors move from said unlocked partially connected position to said locked fully connected position, wherein said hook of said locking tab covers a side of said ramp only when the first and second connectors are in the locked fully connected position, and wherein said indicator is attached to said side of said ramp, wherein when said first and second connectors are moved to said locked fully connected position said hook of said locking tab simultaneously covers said indicator and also locks said first and second connectors together, and wherein said ramp deflects said locking tab away from said second connector to expose said indicator to said camera when said first and second connectors are in a partially connected position.

2. The system as defined in claim 1 wherein said indicator comprises a colored marking different in color than a color of both connectors.

3. The system as defined in claim 1 wherein said connectors are electrical connectors.

4. A method to verify a complete connection of a first and second connector movable relative to each other between a partially connected position and a locked fully connected position comprising the steps of:

placing an indicator on said first connector which becomes hidden from view only when the connectors are in said locked fully connected position, positioning a camera so that the camera generates an output signal representative of the appearance of objects present at an inspection station so that said camera detects the indicator, if visible, when the first and second connectors are at the inspection station, and processing the output signal from the camera with an optical recognition circuit having a processor which determines if the indicator is visible and generating an alarm sign if the connectors are in the partially connected position based upon the presence of the indicator in the camera output signal, wherein said indicator comprises a pattern applied to said first connector, wherein the first connector includes a ramp and the second connector includes a flexible and resilient locking tab having a hook which travels along said ramp as said connectors move from said unlocked partially connected position to said fully locked fully connected position, wherein said hook of said locking tab covers a side of said ramp only when the first and second connectors are in the locked fully connected position, and wherein said indicator is attached to said side of said ramp, wherein when said first and second connectors are moved to said locked fully connected position said hook of said locking tab simultaneously covers said indicator and locks said first and second connectors together, and wherein said ramp deflects said locking tab away from said second connector to expose said indicator to said camera when said first and second connectors are in a partially connected position.

5. The method as defined in claim 4 wherein said indicator comprises a colored marking different in color than a color of both connectors.

6. The method as defined in claim 4 wherein said connectors are electrical connectors.

* * * * *